US00PP37468P2

(12) United States Plant Patent
Hansen

(10) Patent No.: US PP37,468 P2
(45) Date of Patent: Jun. 9, 2026

(54) ***ECHINACEA* PLANT NAMED 'Raspberry Ripple'**

(50) Latin Name: ***Echinacea* hybrid**
Varietal Denomination: Raspberry Ripple

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,861

(22) Filed: Oct. 14, 2025

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
See application file for complete search history.

(56) References Cited

U.S. PATENT DOCUMENTS

PP35,404 P2 * 9/2023 Hansen ..... Plt./428

* cited by examiner

*Primary Examiner* — Susan Mccormick Ewoldt
*Assistant Examiner* — Zachariah Allan Kay

(57) ABSTRACT

The new and distinct cultivar of *Echinacea* plant named 'Raspberry Ripple' producing lightly fragrant inflorescences with nearly horizontal raspberry-pink ray florets and very large disk florets of deep reddish-pink forming a large center pompon. The new plant flowers from mid-summer to late summer, and is suitable as a potted plant, for the landscape, and for cut flower arrangements.

2 Drawing Sheets

Botanical denomination: *Echinacea* hybrid.
Cultivar designation: 'Raspberry Ripple'.

STATEMENT REGARDING PRIOR DISCLOSURES UNDER 37 CFR 1.77(B)(6)

The first offers for sale of the claimed plant were to North Coast Perennials and North Branch Nursery by Walters Gardens, Inc. on Oct. 15, 2024. The first disclosure of the new plant was a photograph and brief description in the "Walters Gardens 2025-2026 Catalog" on Jun. 3, 2025. No plants of *Echinacea* 'Raspberry Ripple' have been sold in this country or anywhere in the world, nor has any disclosure of the new plant been made, more than one year prior to the filing date of this application, and such sale or disclosure within one year was either derived directly or indirectly from the inventor and therefore a 35 U.S.C. § 102(b) exception.

BACKGROUND OF THE INVENTION

The present invention relates to the new and distinct cultivar of Coneflower from the genus *Echinacea* and given the cultivar name 'Raspberry Ripple'. The new plant was the result of a cross by the inventor of an unnamed proprietary hybrid known as 19-3-10 (not patented) as the female parent and an unnamed proprietary hybrid known as 19-3-1 (not patented) as the male in the summer of 2021, at a wholesale perennial nursery in Zeeland, Michigan. The single seedling selected was evaluated initially in trials in the summer of 2022 at the same nursery and assigned the breeder code of 21-7-6.

*Echinacea* 'Raspberry Ripple' has been asexually propagated at the same nursery by crown division and also using careful shoot tip tissue culture procedures and found to reproduce plants that exhibit all the characteristics identical to the original plant in successive generations.

*Echinacea* 'Raspberry Ripple' is distinct from all other Coneflowers known to the inventor. The nearest comparison cultivars are: 'Butterfly Kisses' U.S. Plant Pat. No. 24,458, 'Raspberry Beret' U.S. Plant Pat. No. 35,404, 'Raspberry Truffle' U.S. Plant Pat. No. 22,612, 'Razzmatazz' U.S. Plant Pat. No. 13,894, and 'Secret Affair' U.S. Plant Pat. No. 24,354, 'Strawberry Mousse' (not patented), and 'Watermelon Sugar' U.S. Plant Pat. No. 35,809.

The female parent plant, 19-3-10, has salmon-pink ray florets. The male parent plant, 19-3-1, reddish-pink ray florets and less basal branching.

'Butterfly Kisses' has a shorter and narrower habit, smaller inflorescences with brighter purplish-pink ray florets that droop more. 'Raspberry Beret' has a smaller habit and smaller inflorescences with deeper purplish-red ray florets. 'Raspberry Truffle' has a smaller habit, smaller inflorescences with deep reddish disk florets and smaller ray florets that are brighter purplish-red. 'Razzmatazz' has a much larger upright habit with less basal branching, smaller inflorescences with ray florets that are smaller and more purplish, and disk florets that are not as bright reddish. 'Secret Affair' has slightly smaller inflorescences with ray florets that are shorter and more purplish, and disk florets that are darker reddish. 'Watermelon Sugar' has a slightly larger habit with smaller inflorescences having ray florets that are shorter and more purplish and disk florets that are more purplish-red.

SUMMARY OF THE INVENTION

*Echinacea* 'Raspberry Ripple' has not been evaluated under all possible environmental conditions. The phenotype may vary with variations in the environment including:

growing temperature, available sunlight, nutrients, water, etc. without a change in the genotype of the plant. The new plant is distinct from its parents and all other *Echinacea* known to the applicant in the following combined traits:

1. Lightly fragrant inflorescences with raspberry-pink ray florets;
2. Very large disk florets of deep reddish-pink;
3. Center pompon of disk florets that have notched apices;
4. Vigorous growth habit with strong stems and dark burgundy color;
5. Medium-green ovate foliage.

BRIEF DESCRIPTION OF THE DRAWINGS

The photographs of 'Raspberry Ripple' demonstrate the overall appearance of the plant including the unique traits. The drawings of the new plant are of a two-year-old plant grown in a full-sun trial garden in Zeeland, Michigan. The colors are as accurate as reasonably possible with color reproductions. Some slight variations of color may occur as a result of lighting quality, intensity, wavelength, direction, or reflection.

DETAILED DESCRIPTION OF THE PLANT

Figure 1:
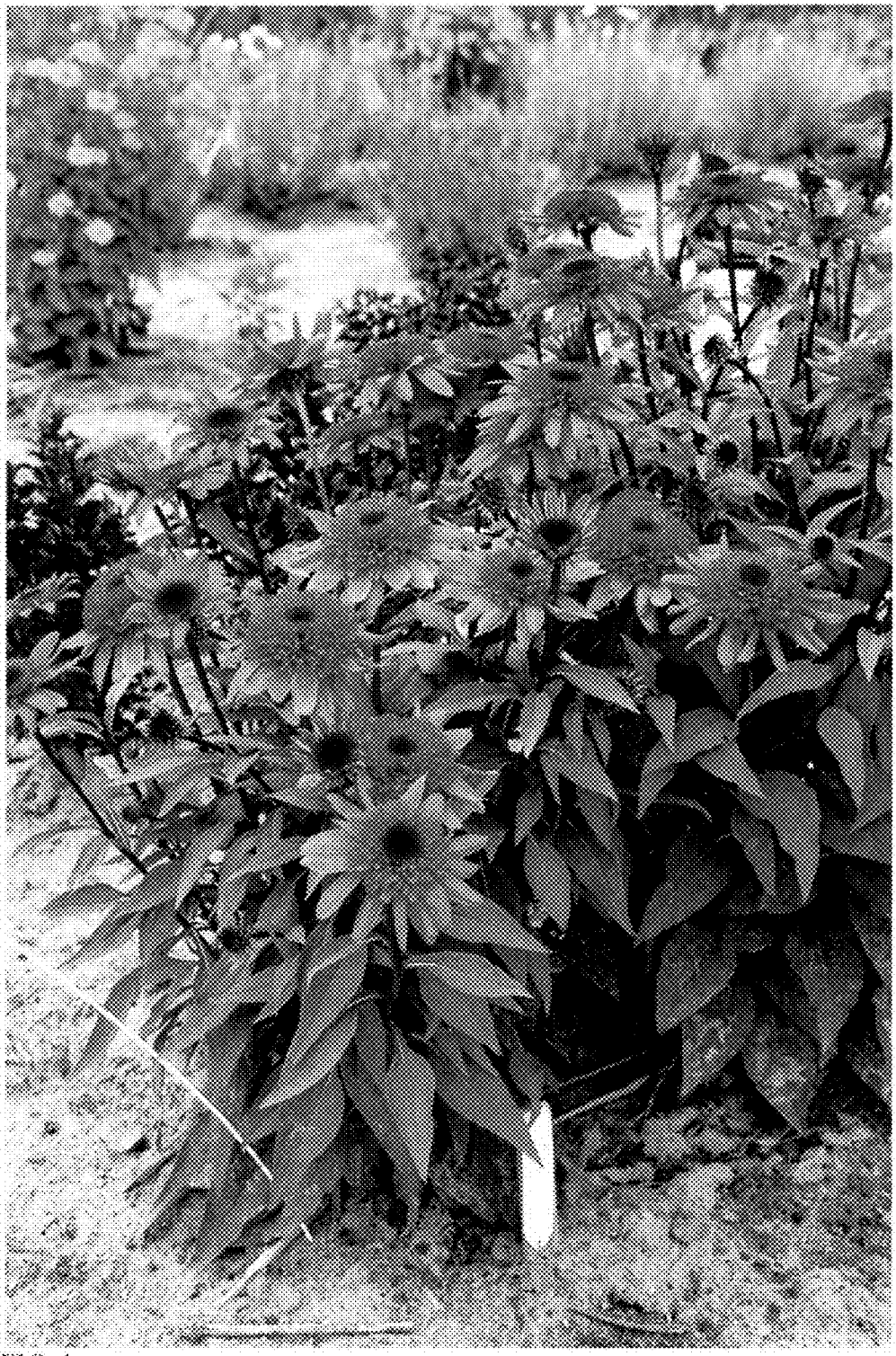
FIG. 1 shows the habit of the new plant in the flower.
Figure 2:
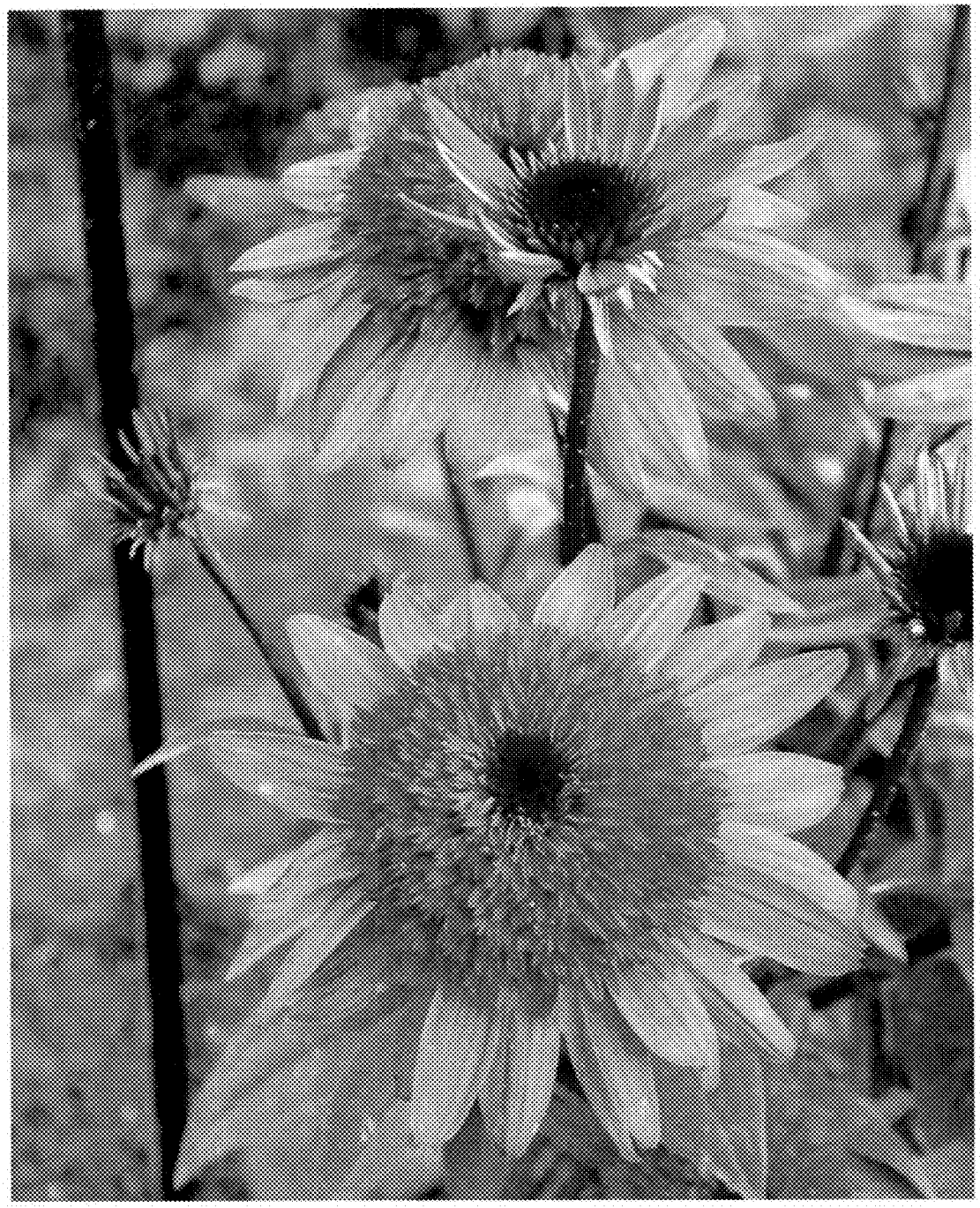
FIG. 2 shows a close-up from above of some inflorescences with flat ray florets and large center pompon.

The following description of *Echinacea* 'Raspberry Ripple' is based on observations of two-year-old specimens grown in a full-sun display garden in Zeeland, Michigan. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female or seed parent is 19-3-10 male or pollen parent is 19-3-1;

Plant habit: Multi-stemmed, freely-branched, hardy herbaceous perennial, flowering to about 58 cm tall and 65 cm wide with foliage to 40 cm tall and 52 cm wide;

Growth rate: Vigorous, finishing in 4-liter containers in about 2 months during the summer;

Roots: Finely-branched; color between RHS 159D and NN155B;

Foliage: Alternate; ovate; acute apex; cuneate base; margin micro-ciliolate and serrulate with teeth to about 2 mm long and 3 mm wide; micro-hirsutulous adaxial and hirsutulous abaxial; to about 21 cm long and 9 cm wide decreasing distally, average about 9.5 cm long and 6 cm wide;

Leaf color: Young leaves adaxial nearest RHS 146B, abaxial nearest RHS 146A; mature leaves adaxial nearest NN137A, abaxial nearest RHS 147B; variegation absent;

Foliage fragrance: Lightly herbal;

Venation: Pinnately three-nerved and reticulate; abaxial midrib and veins costate; glabrous adaxial, hirsutulous abaxial;

Vein color: Adaxial basal midrib and basal primary veins between RHS 193A and RHS 145C, distally nearest RHS NN137A; abaxial proximal midrib between RHS 145B and RHS 146D, distal midrib and primary veins nearest RHS 137B secondary veins nearest RHS NN137B;

Petiole: Concavo-convex; glabrous adaxial; hirsutulous abaxial; to about 12 cm long and 9 mm wide at the semi-clasping base and 2.5 mm wide in middle of lowest leaves and decreasing to nearly sessile distally;

Petiole color: Adaxial base nearest RHS 71A, abaxial base nearest RHS 186A, adaxial midrib between nearest RHS 186A and the margins 145D and RHS 146D; abaxial midrib between RHS 145D and RHS 145C, and the abaxial margins nearest RHS NN137C;

Stem: Hirsutulous; cylindrical; strong and stiff; to about 40 cm long including peduncle and about 9 mm diameter at base; average 36 cm long and 6 mm diameter; about 12 per plant; aspect upright;

Stem color: Nearest RHS 146C;

Peduncle: Hirsutulous to pubescent; terete; strong; stiff; heavily branched; about 7 cm long and 6 mm diameter above last leaves; quantity per stem about six to nine; aspect ascending to slightly outwardly;

Peduncle color: Proximally nearest RHS 147B and nearest RHS 187A in high light exposure;

Internode: 9 to 11 per stem; average about 3.6 cm long, shorter proximally and longer distally; node color same as surrounding peduncle;

Branches: Cylindrical; hirsutulous; tightly angled to main stem to about 60° above horizontal: about 5 to 7 branches per stem; to about 20 cm long and 6 mm diameter;

Branch color: Proximally nearest RH$ 187B;

Inflorescence: Bracteate head, aggregate of achene; with single whorl of distinct ligulate ray florets and enlarged disk florets above pappus producing a pompon effect; flowering mid-summer to late summer; initial inflorescence largest, to about 12.5 cm wide and 7.5 cm tall, with inner pompon to 7.2 cm across and 5.5 cm tall; to 6 to 9 inflorescences per stem;

Inflorescence fragrance: Lightly sweet, honey-like;

Flower persistence: Remaining effective in color for 14 to 18 days depending on temperatures, cone drying on plant, and effective into winter;

Involucre: With numerous bracts, about 38 to 62 per inflorescence in 3 to 4 whorls; reflexed toward peduncle;

Involucre bracts: Deltoid; acute apex; truncate base; micro-ciliolate margin; reflexed; adaxial glabrous; abaxial micro-hirsutulous; to about 15 mm long and 5 mm across;

Involucre bract color: Adaxial and abaxial center nearest RHS 137A, adaxial and abaxial edges nearest RHS 145B;

Inflorescence buds with ray florets vertical and still enrolled: About 32 mm across and 23 mm tall; ray floret color between RHS 186B and RHS N186C, disk florets nearest RHS 187B, and spines nearest RHS 187A;

Ray florets: Sterile; lignlate; zygomorphic; arrangement in single whorl, frequently moderately imbricate; apex emarginated with two notches, rarely three notches, to about 1 mm deep; base attenuate; margin entire; adaxial and abaxial surfaces matte; 16 to 21 per inflorescence; opening to horizontal, drooping up to 30 degrees below horizontal with maturity; flat, twisting absent; sterile; ray floret to 57 mm long and 18 mm wide near middle, base to about 3 mm wide; average size 53 mm long and 16 mm wide at center tapering to 2.5 mm wide at base; adaxial veins variably, sometimes thickened and raised;

Ray floret color: Changing with maturity; when first horizontal young adaxial between RHS 53A and RHS 53B in the distal two-thirds, in the proximal one-third with regions nearest RHS 32C, RHS 61A, and between RHS 53B and RHS 53C, with the basal claw nearest RHS 36B with an undertone of nearest RHS 146D; when first horizontal young abaxial distal three-quarters between RHS 60C and RHS 60D, in the proximal one-quarter near between RHS 62D and RHS 63D, with the claw between RHS 145C and RHS 145D; before dropping adaxial the distal one-half between RHS 182B and RHS 185D, next proximal 1.5 cm between RHS 185C and RHS 186B, and basal claw nearest RHS 145C; before dropping abaxial claw nearest RHS 145C and distal portion between RHS 185D and RHS 186D;

Disk florets: About 400 to 500 per inflorescence; zygomorphic; perfect; produced in large raised dome pompon to 7.2 cm across and 5.5 cm tall, individually to about 29 mm long and 8 mm wide;

*Disk floret corolla*.—Typically five tepals fused forming tube; to about 27 mm long and 8 mm wide near middle, fused in tube in basal 2 mm, free in distal 25 mm; individual tepals about 2 mm wide at fusion; truncate emarginate apex with two to three notches to about 5 mm long with lobes having acute apices; entire margin; both surfaces matte; pappus.

*Disk floret corolla tube color*.—When ray florets initially opened flat adaxial distally nearest RHS 53A, in the middle nearest RHS 46D, with base nearest RHS 145C; abaxial apex nearest RHS 53A, middle between RHS 49A and RHS 49B with base between RHS 145D and RHS 145C; with maturity before drying adaxial distally nearest RHS 59A, middle portion between RHS 157A and RHS 158A, proximally nearest RHS 145C; with maturity abaxial between RHS 187B and RHS 187C, middle portion between RHS 185D and RHS NN155A, base nearest RHS 145C.

*Androecium*.—Present on disk florets only; five; synandrous.

*Staminal column*.—About 0.7 mm wide, about 3 mm long and not exserted; five fused stamens.

*Anthers*.—Fused, about 2 mm long and 0.7 mm diameter; color nearest RHS N186A when present.

*Filaments*.—Five; attached to column; thin, less than 0.2 mm diameter and 1 tom long; color nearest RHS N155D.

*Pollen*.—Not observed.

*Gynoecium*.—Present on disk florets only; single; to 10 mm long.

*Style*.—Cylindrical; single main or split with up to three smaller branches; to about 4 mm long and 0.2 mm diameter; color between RHS 155A and RHS 160D.

*Stigma*.—Bifid; about 1 mm long and 0.1 mm diameter; color nearest RHS 181B.

*Ovary*.—Inferior; obdeltoid; to 3.5 mm long and 2 mm wide at apex; color nearest RHS 155C.

*Fruit*.—Obdeltoid; to 4 mm long and 3 mm wide at apex; color nearest RHS 199D.

Pappus: Above fruit; apex fimbriate; to about 1.5 mm long and 2 mm across at apex; color as developing nearest RHS 145C, when dried nearest RHS 199C;

Receptacle spines: With disk florets; acicular; narrowly acute apex; glabrous; lustrous; to 18 mm long and 2 mm across near middle; producing a cone about 50 mm wide and 30 mm tall;

Spine color: Adaxial and abaxial apices or distal 2 mm nearest RHS 187A, next proximal 2 mm nearest RHS 175C, middle portion nearest RHS 146C, proximal portion between RHS 145D and RHS N144A, base nearest RHS 155C;

Disease resistance: Resistance and susceptibility beyond that of other hardy Coneflower cultivars have not been observed.

Growth: The plant grows best with plenty of moisture and adequate drainage but is able to tolerate some drought when mature.

Winter hardiness: At least from USDA zone 4 through 8.

I claim:

1. A now and distinct cultivar of *Echinacea* plant named 'Raspberry Ripple' as herein described and illustrated.

* * * * *